United States Patent
Collings et al.

(10) Patent No.: US 11,666,709 B2
(45) Date of Patent: Jun. 6, 2023

(54) DRIVE MECHANISM WITH NOISE REDUCTION

(71) Applicant: SANOFI, Paris (FR)

(72) Inventors: Ralph Donald Quentin Collings, Bristol (GB); James Robert Coop, Bristol (GB); James Anthony West, Bristol (GB); Stephen Francis Gilmore, Bristol (GB); Daniel David Higgins, Bristol (GB); Mark Digby Teucher, Bristol (GB); Jack Carroll, Bristol (GB); Timothy Robin Quigg, Bristol (GB); Laura Stein, Frankfurt am Main (DE); Stefan Blancke, Frankfurt am Main (DE); Sophie Sladen, Warwick Warwickshire (GB)

(73) Assignee: Sanofi, Paris (FR)

( * ) Notice: Subject to any disclaimer, the term of this patent is extended or adjusted under 35 U.S.C. 154(b) by 422 days.

(21) Appl. No.: 16/771,151

(22) PCT Filed: Dec. 20, 2018

(86) PCT No.: PCT/EP2018/086121
§ 371 (c)(1),
(2) Date: Jun. 9, 2020

(87) PCT Pub. No.: WO2019/122085
PCT Pub. Date: Jun. 27, 2019

(65) Prior Publication Data
US 2021/0170111 A1    Jun. 10, 2021

(30) Foreign Application Priority Data
Dec. 21, 2017   (EP) .................................... 17306877

(51) Int. Cl.
*A61M 5/20* (2006.01)
*A61M 5/315* (2006.01)
*A61M 5/31* (2006.01)

(52) U.S. Cl.
CPC .... *A61M 5/31583* (2013.01); *A61M 5/31553* (2013.01); *A61M 2005/3143* (2013.01);
(Continued)

(58) Field of Classification Search
CPC .......... A61M 5/31583; A61M 5/31553; A61M 2005/3143; A61M 2005/3152;
(Continued)

(56) References Cited

U.S. PATENT DOCUMENTS

| 2002/0108831 A1 | 8/2002 | Pawley |
| 2004/0210199 A1 | 10/2004 | Atterbury et al. |

(Continued)

FOREIGN PATENT DOCUMENTS

| CN | 106794317 | 5/2017 |
| CN | 106999673 | 8/2017 |

(Continued)

OTHER PUBLICATIONS

PCT International Search Report and Written Opinion in International Appln. No. PCT/EP2018/086121, dated Mar. 19, 2019, 12 pages.
PCT International Preliminary Report on Patentability in International Appln. No. PCT/EP2018/086121, dated Jun. 23, 2020, 9 pages.

*Primary Examiner* — Amber R Stiles
*Assistant Examiner* — Nelson Louis Alvarado, Jr.
(74) *Attorney, Agent, or Firm* — Fish & Richardson P.C.

(57) ABSTRACT

A drive mechanism for a drug delivery device with a reduced operating loudness includes a dose selector, a housing, and a ratchet with a gear element comprising a plurality of gear teeth connected with the dose selector and a pawl element rotationally constrained to the housing comprising at least (Continued)

one pawl tooth. The at least one pawl tooth engages with the gear teeth and is located opposite to the gear teeth. One of the gear element and the pawl element moves forth and back relative to the other element of the gear and pawl elements along a first direction for de-engagement and re-engagement of the opposite gear teeth and at least one pawl tooth when the gear element rotates relative to the housing during dose setting using the dose selector. The pawl element and/or gear element comprises a noise reduction characteristic at a surface which dampens the noise produced.

20 Claims, 14 Drawing Sheets

(52) U.S. Cl.
CPC ............... *A61M 2005/3152* (2013.01); *A61M 2205/0216* (2013.01); *A61M 2205/0222* (2013.01); *A61M 2205/42* (2013.01)

(58) Field of Classification Search
CPC .. A61M 2205/0216; A61M 2205/0222; A61M 2205/42; A61M 5/31535; A61M 5/31541; A61M 5/20
See application file for complete search history.

(56) References Cited

U.S. PATENT DOCUMENTS

| | | |
|---|---|---|
| 2005/0274216 A1 | 12/2005 | Fleytman |
| 2006/0097026 A1 | 5/2006 | Shelton |
| 2008/0164354 A1 | 7/2008 | Huang |
| 2008/0319394 A1* | 12/2008 | Yodfat ................ F04B 43/1253 604/154 |
| 2015/0119816 A1 | 4/2015 | Helmer |
| 2016/0235923 A1 | 8/2016 | Plumptre et al. |
| 2016/0346480 A1 | 12/2016 | Gleason et al. |
| 2017/0312447 A1 | 11/2017 | Marsh et al. |

FOREIGN PATENT DOCUMENTS

| | | |
|---|---|---|
| JP | H10-504672 | 5/1998 |
| JP | 2015-537159 | 12/2015 |
| JP | 2017-530799 | 10/2017 |
| WO | WO 1995/034068 | 12/1995 |
| WO | WO 2014/072298 | 5/2014 |
| WO | WO 2014/092973 | 6/2014 |
| WO | WO 2016/055624 | 4/2016 |
| WO | WO 2016/091978 | 6/2016 |

* cited by examiner

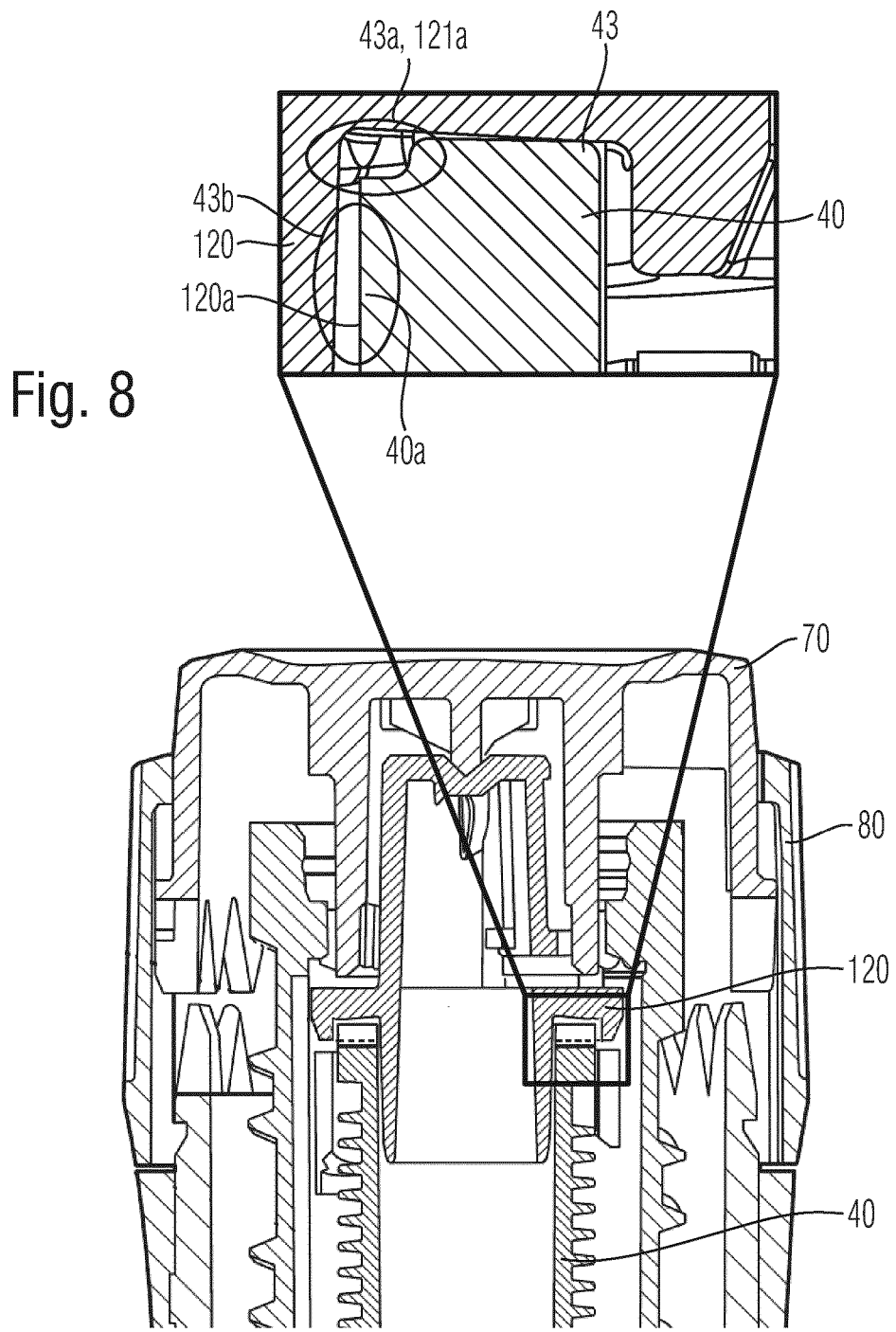

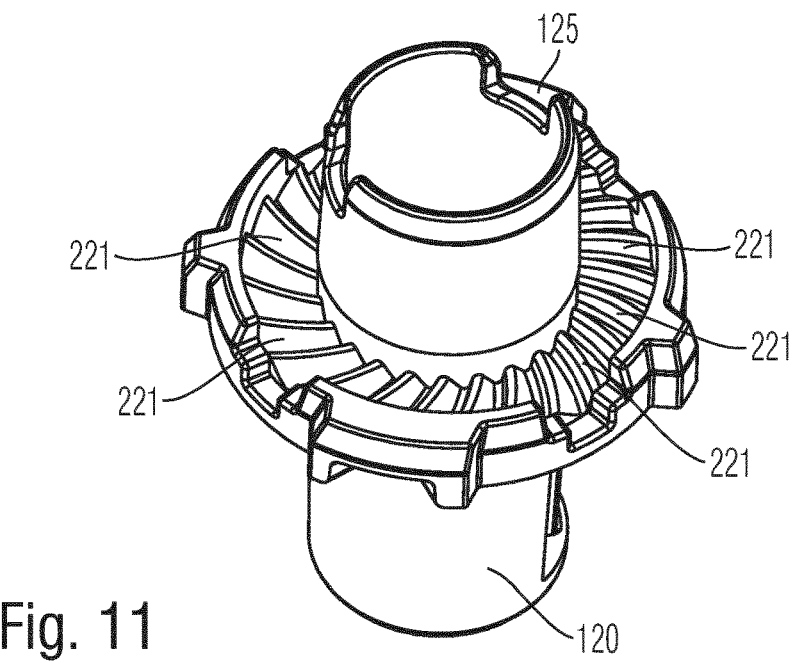
Fig. 11
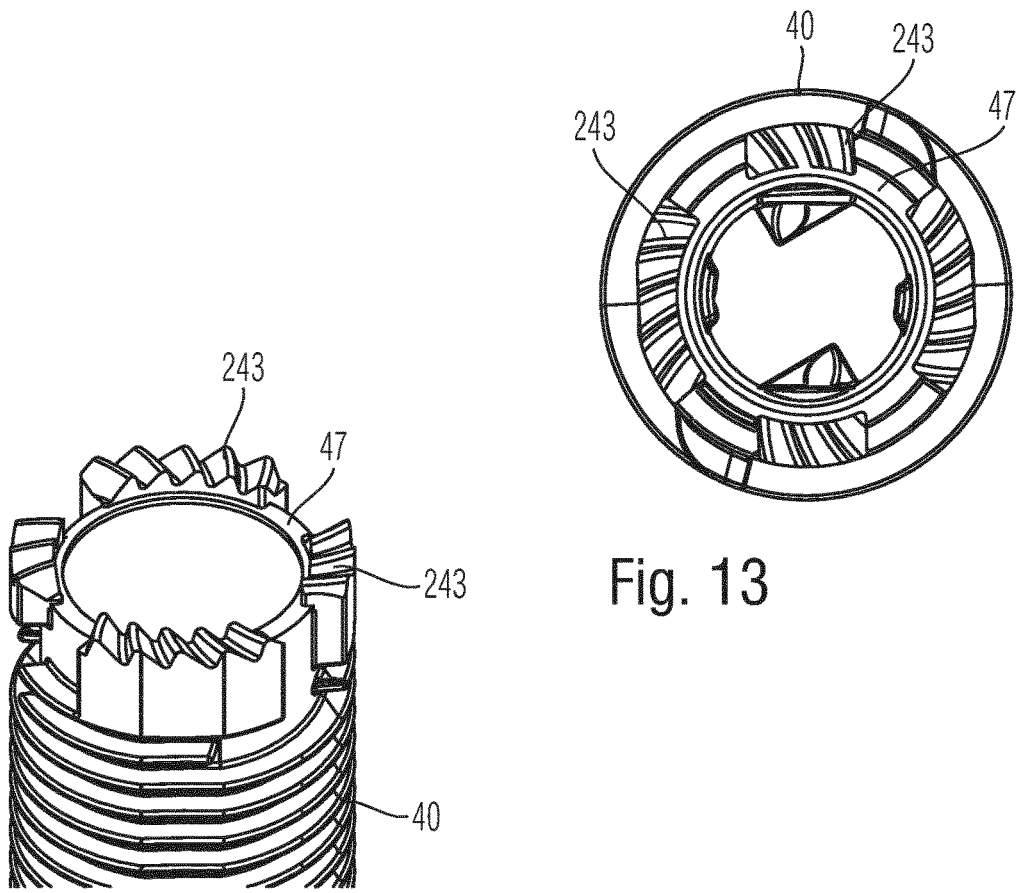
Fig. 13
Fig. 12

DRIVE MECHANISM WITH NOISE REDUCTION

CROSS REFERENCE TO RELATED APPLICATIONS

The present application is the national stage entry of International patent Application No. PCT/EP2018/086121, filed on Dec. 20, 2018, and claims priority to Application No. EP 17306877.6, filed on Dec. 21, 2017, the disclosures of which are incorporated herein by reference.

TECHNICAL FIELD

The present disclosure relates to a drive mechanism for a drug delivery device, especially a pen type drug delivery device for selecting and dispensing a number of user variable doses of a medicament. Further, the disclosure relates to such a drug delivery device.

BACKGROUND

The drive mechanism comprises a dose selector, a housing and a ratchet with a gear element comprising a plurality of gear teeth connected with the dose selector and a pawl element rotationally constrained to the housing comprising at least one pawl tooth, wherein the at least one pawl tooth engages with the gear teeth and is located opposite to the gear teeth, wherein one of the gear element and the pawl element moves forth and back relative to the other element of the gear element and the pawl element along a first direction for de-engagement and re-engagement of the opposite gear teeth and at least one pawl tooth when the gear element rotates relative to the housing during dose setting using the dose selector, i.e. dose dialing. The ratchet teeth that are allowed to be overridden during dose setting, when the user rotates the dose selector to increase or decrease the dose, produce a noise which is transmitted along the drug delivery device and which is perceived too loud.

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges.

Rather, the pre-filled cartridges may not be removed and replaced from these devices without destroying the device itself. Consequently, such disposable devices need not have a resettable dose setting mechanism.

These types of pen delivery devices (so named because they often resemble an enlarged fountain pen) generally comprise three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, which is often initiated by actuating a button, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

SUMMARY

It is an object of the present disclosure to provide a drive mechanism and a drug delivery device with a reduced operating loudness.

This object is solved by a drive mechanism with the features of claim 1 and a drug delivery device with the features of claim 13.

In particular, the drive mechanism for a drug delivery device comprises a dose selector, a housing and a ratchet (also referred to as first clutch) with a gear element comprising a plurality of gear teeth connected with the dose selector and a pawl element rotationally constrained to the housing comprising at least one pawl tooth, wherein the at least one pawl tooth engages with the gear teeth and is located opposite to the gear teeth, wherein one of the gear element and the pawl element moves forth and back relative to the other element of the gear element and the pawl element along a first direction for de-engagement and re-engagement of the opposite gear teeth and at least one pawl tooth when the gear element rotates relative to the housing during dose setting the dose selector, wherein the pawl element and/or the gear element comprises a noise reduction characteristic at its/their surface, for example at at least a part of its/their surface, which dampens the noise produced when the tooth or teeth of the respective other element of the pawl element and the gear element move(s) back into re-engagement when the gear element rotates relative to the pawl element.

The noise reduction characteristic dampens the noise which is caused by the hit of one tooth or plurality of teeth of the ratchet (i.e. the gear teeth or the at least one pawl tooth) during re-engagement with the next detented position.

The audible sound produced by the hit is reduced by the noise reduction characteristic for which different examples are provided in the following.

The noise reduction may be provided by grease located at at least a part of the surface of the gear teeth or of the at least one pawl tooth, by a form change of the ratchet teeth or by an elastomeric material provided at at least a part of the surface of the gear teeth or of the at least one pawl tooth formed by a surface layer or a body consisting of the elastomeric material.

According to one embodiment of the disclosure the first direction is a longitudinal direction of the drive mechanism or a direction radial to the longitudinal direction.

In one embodiment the pawl element is rotationally constrained to the housing during dose dialing only, whereas during dose application the pawl element may rotate, for example with the drive sleeve with respect to the housing.

In one embodiment the drive mechanism comprises a spring driven rotatable drive member, a rotatable driven member, a clutch/ratchet for rotationally coupling the driven member and the drive member in a coupled state and allowing relative clockwise and/or anti-clockwise rotation between the driven member and the drive member in a decoupled state, and a (clutch) spring biasing the clutch into its coupled state and allowing relative axial movement between the drive member and the driven member into the decoupled state of the clutch against the bias of the spring.

Further, in one embodiment the pawl element is located at the driven member in form of the drive sleeve, for example at a front surface of the drive sleeve, i.e. at its proximal end. The gear element may be located at the drive member, for example a front surface of a clutch plate. The drive sleeve is rotationally constrained with respect to the housing during dose setting. The teeth of the ratchet, namely the gear teeth and the at least one pawl tooth may be arranged such that it provides detented position between the clutch plate and the drive sleeve corresponding to one dose unit, and engages different ramped tooth angles during unrestricted rotation, e.g. during dose setting when increasing the dialed dose, and during less unrestricted rotation or restricted rotation, e.g. during dose setting when decreasing the dialed dose. For example, as the user rotates the dose selector sufficiently to increment the mechanism by one dose unit the gear element may be rotated by one ratchet tooth. At this point, the ratchet teeth (i.e. the gear teeth and the at least one pawl tooth) re-engage into the next detented position. An audible click is generated by the ratchet re-engagement, and tactile feedback may be given by the change in torque input required by the user.

According to one embodiment the gear element is located at a front surface of the drive member, i.e. at its distal end, in form of a clutch plate which is rotationally constrained with respect to the dose selector during dose setting. Further, the drive sleeve or the clutch plate may be biased in longitudinal direction against the dose selector or the clutch plate or housing, for example by a compression spring in the following also referred to as clutch spring. The dose selector may additionally be splined According to one aspect the noise reduction characteristic comprises grease located at the surface of the gear teeth or the at least one pawl tooth, preferably at an inner section near the longitudinal axis of the drive mechanism. In one embodiment the grease partially fills space between edge of the pawl teeth, e.g. the drive sleeve pawl teeth, and the gear teeth inner section, e.g. the clutch plate gear teeth. Higher volume of grease reduces loudness but may reduce crispness of click as well during dose setting. The amount of grease may be optimized in order to balance loudness reduction and crispness reduction. Sound improvement appears most effective if grease is either applied in multiple 'spots' around circumference of the gear element or pawl element, or spread equally around circumference.

Grease with high viscosity is particularly suitable.

In one embodiment the grease may be located for example
  directly between the clutch plate gear teeth and drive sleeve pawl teeth,
  at the clutch plate/button bearing surface, and/or
  at the drive spring outer surface.

The volume of grease, the interfaces, the pattern of application (e.g. applied in one spot or two spots or more spots or spread across a surface) all effect the magnitude of loudness reduction and can be tailored to provide the optimum balance between loudness and "crispness" of click with regard to the particular drive mechanism.

According to another aspect the noise reduction characteristic comprises a helical form of the gear teeth and a corresponding helical form of the at least on pawl tooth. This has the advantage, that, when helical teeth meet, the contact area spreads gradually as the teeth move closer together. This progressive tooth interaction spreads the impact of the ratchet over a longer time period and distribute the load more evenly. The reduced force involved in the impact reduces the amplitude of the sound emitted at this interface.

According to another aspect the noise reduction characteristic comprises a beveled form of the gear teeth and a corresponding beveled form of the at least on pawl tooth. In this embodiment the gear teeth and the at least one pawl tooth are straight teeth. This embodiment has the advantage that the conical contact of a bevel design may reduce 'impact' upon teeth engagement. It was thought taper-fit nature of mating parts may increase contact time, decreasing impact energy due to dissipating energy over a larger time period.

In one embodiment the beveled form of the gear teeth is such that the height of the teeth at the inner section near the longitudinal axis is greater than at the outer section further away from the longitudinal axis of the drive mechanism.

According to another aspect the noise reduction characteristic comprises an elastomeric material surface layer or elastomeric material body at a predefined section of at least part of the gear teeth and/or the at least one pawl tooth. The predefined section of the gear teeth and/or the at least one pawl tooth may comprise the front side of the gear teeth and/or the at least one pawl tooth, the back side of the gear teeth and/or the at least one pawl tooth, a section of the radial length of the gear teeth and/or the at least one pawl tooth and/or a part of the whole number of gear teeth and/or the at least one pawl tooth, for example every second or third tooth.

For example, alternate teeth on the clutch plate would be co-molded in an elastomeric material which would reduce the impact volume by two methods:
  Some teeth on the drive sleeve would impact a soft surface which dissipates the kinetic energy through movement and heat.
  The elastomeric material would dampen the part, reducing the time for which the noise rings out.

The elastomeric teeth would be fractionally advanced over those which are a rigid, ensuring that the initial contact of ratchet teeth is with the soft, rubberized surface.

Regarding the present disclosure, the elastomeric material is, for example, an injection moldable rubber mixture or thermoplastic elastomer (TPE), the elastomeric material may consist of, for example, one or more compositions of the group comprising styrenic block copolymers (TPE-s or TPS), thermoplastic olefins (TPE-o or TPO), elastomeric alloys (thermoplastic vulcanizates, TPE-v or TPV), thermoplastic polyurethanes (TPE-u or TPU), thermoplastic copolyester (TPE-E or TPC) and thermoplastic polyamides (TPE-A or TPA).

The material of the gear teeth and/or the at least one pawl tooth may for example, consist of one or more compositions of the group comprising PC (polycarbonates), PBT (Polybutylene terephthalates) and POM (Polyoxymethylene).

According to another aspect the noise reduction characteristic comprises an annular collar attached at the gear element or at the pawl element with a plurality of pawl teeth, wherein the annular collar comprises a plurality of collar teeth formed by an elastomeric material, wherein one collar tooth forms an outer section of one gear tooth or one pawl tooth. In one embodiment part of the gear teeth or pawl teeth are shortened and complemented by one collar tooth. The shortened gear tooth or the shortened pawl tooth forms the inner section of the combined tooth whereas the outer section with a greater distance from the longitudinal axis of the mechanism is formed by the respective collar tooth. In other words: The gear tooth or pawl tooth located in radial direction next to the collar tooth forming together a combined tooth consists of different materials. The material located at the outer section (i.e. the material of the collar tooth) is more elastic than the material of the inner section (i.e. the material of the gear tooth or the pawl tooth) of the combined tooth. Such combined tooth may have an overall helical form or an overall beveled form as described above. The gear teeth or pawl teeth forming the inner section of the ratchet teeth may be spaced equally in a predefined number (e.g. 4) of clusters around the circumference, wherein each cluster may, for example, comprise 2, 3, 4 or 5 teeth.

In one embodiment the annular collar comprises two concentric rings (or hollow cylinders), one inner ring and one outer ring, wherein the inner ring is attached to the outer ring by at least two radial webs. At least one cavity, e.g. having an arcuate form, is formed between the inner ring and the outer ring of the annular collar. In one embodiment the outer ring comprises the collar teeth at its upper surface. The annular collar may be attached to the gear element or the pawl element such that the gear teeth or the pawl teeth project through the at least one cavity formed between the inner ring and the outer ring.

According to another aspect the noise reduction characteristic comprises an internal bung attached at the gear element or at the pawl element comprising a plurality of pawl teeth, wherein the internal bung comprises a plurality of bung teeth elements formed by an elastomeric material, wherein the bung teeth elements replace at least one of the gear teeth or the pawl teeth.

In one embodiment the gear teeth or pawl teeth may be spaced equally in a predefined number (e.g. 4) of clusters around the circumference, wherein each cluster may, for example, comprise 2, 3, 4 or 5 teeth. Between two neighboring clusters of gear teeth or pawl teeth at least one bung tooth element is located at the circumference.

In one embodiment the bung comprises a pot-like circular body which is formed as a U in cross-section with a cylindrical section and a plate-like base section, wherein the upper rim of the bung body comprises the bung teeth at its outer surface. The plate-like base section may have a through-going hole. The bung teeth may be located at the upper rim of the cylindrical section opposite to the base section. The strong internal bung may be attached to the gear element or the pawl element such that the gear teeth or the pawl teeth complete the circular circumference with the bung teeth elements. The circular body is located at the inner section of the bung teeth elements and the gear teeth or the pawl teeth. In one embodiment in which the pawl element is formed by the front face of the drive sleeve the internal bung is put into the inner cavity of the drive sleeve.

According to another aspect the noise reduction characteristic comprises a damping hoop attached at the gear element or at the pawl element comprising a plurality of hoop teeth elements, wherein the internal bung comprises a plurality of hoop teeth elements formed by an elastomeric material, wherein the hoop teeth elements replace at least one of the gear teeth or the pawl teeth.

In one embodiment the gear teeth or pawl teeth may be spaced equally in a predefined number (e.g. 4) of clusters around the circumference, wherein each cluster may, for example, comprise 2, 3, 4 or 5 teeth. Between two neighboring clusters of gear teeth or pawl teeth at least one hoop tooth element is located at the circumference.

In one embodiment the damping hoop comprises two concentric rings (or hollow cylinders), one inner ring and one outer ring, wherein the inner ring is attached to the outer ring by at least two radial webs. At least one cavity, e.g. having an arcuate form, is formed between the inner ring and the outer ring of the damping hoop. In one embodiment the at least two radial webs comprise the hoop teeth elements at their upper surface. The damping hoop may be attached to the gear element or the pawl element such that the gear teeth or the pawl teeth project through the at least one cavity formed between the inner ring and the outer ring. The hoop teeth elements and the gear teeth or the pawl teeth form together a full circumference.

In another embodiment the bung teeth element and the hoop teeth element is one of a straight tooth corresponding in its form to the teeth it replaces, a notched section, a crab claw section, and a pebble projection.

In one embodiment the notched section is a notched projection or land, for example in cuboid form running along the circumference of the gear element or the pawl element, wherein the form of the notched bung resembles one cut-off tooth-cut in its height.

In one embodiment the crab claw section is a rim-like section running along the circumference of the gear element or the pawl element, wherein the rim has a radial cross section which is smaller than the radial cross section of the pawl teeth or the gear teeth it replaces. Two concentric or parallel rim-like sections may be used as well. The crab claw section is located approximately at the half of the radial width of the neighboring gear teeth or pawl teeth. If the crab claw section replaces two or more neighboring gear teeth or pawl teeth there may be no notch along this section.

In one embodiment the pebble projection is a projection from the surface of the pawl element or the gear element forming a cut pebble or sphere section.

In another embodiment the pawl element, i.e. the drive sleeve, comprises a proximal end section formed as a hollow cylinder, wherein the pawl teeth are located at the outer face of the hollow cylinder, wherein the most proximal section of the pawl teeth exceed in height over the proximal face of the hollow cylinder. The pawl teeth may be grouped in clusters of two, three, four, five or more pawl teeth, wherein each cluster has a certain pre-defined distance from the next cluster along the outer rim of the hollow cylinder.

The problem is further solved by a drug delivery device comprising the above-described drive mechanism.

The ratchet according to the disclosure is a characteristic or feature suitable for connecting two characteristic parts either by form fit (positive fit), e.g. with teeth suitable for engaging and disengaging each other, or by a non-positive (frictional) connection or a combination thereof. Actuation of the ratchet, i.e. the act of coupling or decoupling, may include a relative movement of ratchet parts or ratchet features, for example for disengaging ratchet teeth (i.e. the gear teeth and the at least one pawl tooth), and/or may include a change in a force exerted on ratchet parts or ratchet features.

In a preferred embodiment of the disclosure, the drive mechanism further comprises a torsion spring which is directly or indirectly coupled to the drive member such that rotation of the drive member in a first rotational direction charges (strains) the spring and that rotation of the drive member in a second, opposite rotational direction discharges (releases) the spring. To reduce the torque necessary to overhaul the ratchet during dose setting, while preventing unintended discharging of the torsion spring, the pawl teeth and/or gear teeth may have a steeper ramped tooth angle in the second rotational direction and have a shallower ramped tooth angle in the first rotational direction. In addition or as an alternative, the teeth may have a higher friction coefficient in the second rotational direction and have a lower friction coefficient in the first rotational direction.

The drive member may be a separate characteristic part which is rotationally constrained to a dose setting member, e.g. a number sleeve or a dose selector. The drive member may be rotatable and axially constrained, e.g. to a housing, or may be rotatable along a helical path. The driven member may be a tubular element located e.g. inside the number sleeve. On the other hand, the driven member may drive a further characteristic part, for example a piston rod.

A drug delivery device for selecting and dispensing a number of user variable doses of a medicament preferably comprises a drive mechanism as defined above and a piston rod engaging the driven member, wherein the drive member is operatively interposed between the driven member and the dose selector.

The drug delivery device may further comprise a second clutch for rotationally coupling and decoupling the driven member and the housing. Preferably, the driven member is axially displaceable relative to the housing between a first position in which the second clutch rotationally couples the driven member and the housing and a second position in which the second clutch rotationally decouples the driven member from the housing. In other words, the drug delivery device may be switched between a dose setting (or correcting) state in which rotation of the driven member is prevented and a dose dispensing state in which rotation of the driven member is allowed by axial movement of the driven member. In this respect, a button may be provided acting directly or indirectly on the driven member for axial displacement, e.g. against the bias of the clutch spring.

When switching between the dose setting (or correcting) state and the dose dispensing state it is desirable to avoid uncontrolled movement of the driven member, especially in embodiments where the driven member is coupled to a piston rod or the like effecting dose dispensing. Such uncontrolled movement of the driven member could result in amending the set dose prior to dispensing, i.e. underdosage or overdosage. To avoid uncontrolled movement of the driven member the teeth of the clutch are preferably in its coupled state when the driven member and the housing are decoupled by the second clutch. Further, the driven member and the housing are preferably coupled by the second clutch when the teeth of the clutch are in its decoupled state. In other words, the driven member is permanently coupled to at least one of the drive member and the housing.

Further, the drug delivery device may comprise a cartridge containing a medicament. The term "medicament" or "medicament formulation", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4. More details on exendin-4 and its derivatives are provided in the disclosure of the co-pending application PCT/EP2018/082640 which, to this extent, shall be included by reference herein.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N—(ω-carboxyheptadecanoyl)-des(B30) human insulin and B29-N—(ω-carboxyheptadecanoyl) human insulin.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and ρ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF FIGURES

Non-limiting, exemplary embodiments of the aforementioned working principles will now be described with reference to the accompanying drawings, in which:

FIG. 7 shows a sectional view of the proximal end of the device of FIG. 1;

FIG. 8 shows an enlarged detail of FIG. 7;

FIG. 11 shows a perspective side view of a clutch plate of a third embodiment of a drive mechanism;

FIG. 12 shows a perspective side view of a drive sleeve of the third embodiment of a drive mechanism;

FIG. 13 shows a top view of the drive sleeve of FIG. 12;

DETAILED DESCRIPTION

Figure 1:
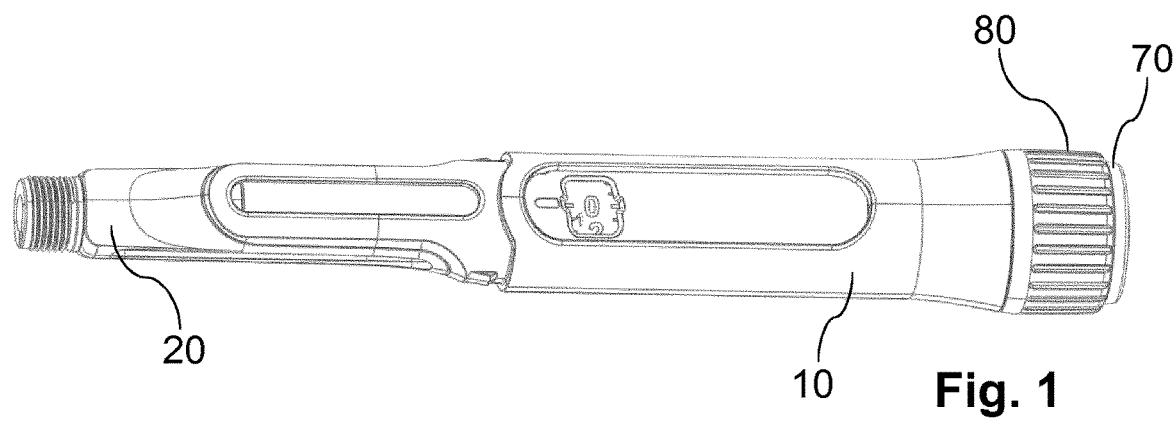
FIG. 1 shows a top view of a first embodiment of a drug delivery device with a first embodiment of a drive mechanism.
Figure 2:
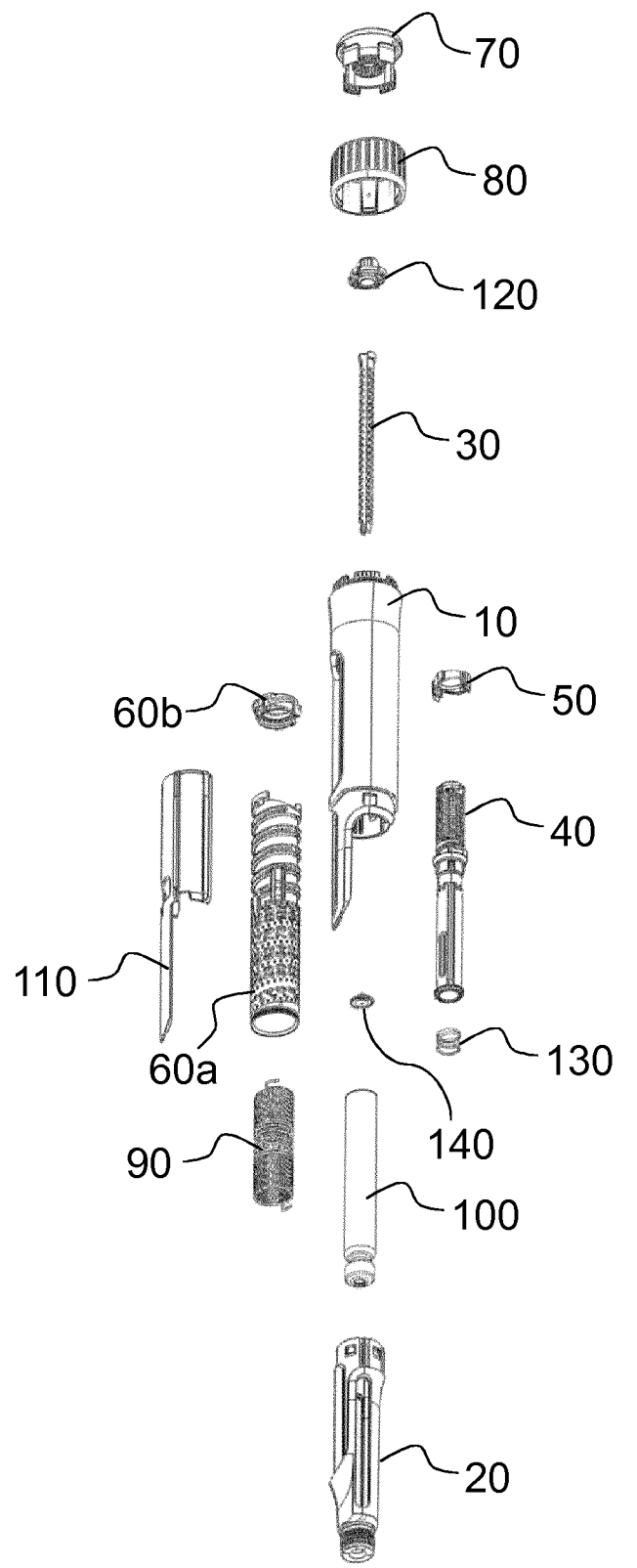
FIG. 2 shows an exploded view of the characteristics of the device of FIG. 1.

FIG. 1 shows a drug delivery device in the form of an injection pen. The device has a distal end (left end in FIG. 1) and a proximal end (right end in FIG. 1). The characteristic parts of the drug delivery device are shown in FIG. 2. The drug delivery device comprises a body or housing 10, a cartridge holder 20, a lead screw (piston rod) 30, a drive sleeve 40, a nut 50, a dose indicator (number sleeve) 60, a button 70, a dial grip or dose selector 80, a torsion spring 90, a cartridge 100, a gauge element 110, a clutch plate 120, a clutch spring 130 and a bearing 140. A needle arrangement (not shown) with a needle hub and a needle cover may be provided as additional characteristics, which can be exchanged as explained above. All characteristics are located concentrically about a common principal axis of the mechanism.

As will be explained in more detail below, the clutch plate 120 is a spring driven rotatable drive member driving the drive sleeve 40 during dose dispensing to rotate relative to the housing 10 to thereby advance piston rod 30. The clutch plate 120 is in turn driven by the number sleeve 60 to which it is rotationally constrained which is attached to one end of the torsion spring 90. On the other hand, although driving the piston rod 30 during dose dispensing, the drive sleeve 40 may be regarded as a driven member because it is driven by the clutch plate 120 (and the number sleeve 60 and the torsion spring 90) during dose dispensing.

The housing 10 or body is a generally tubular element having a proximal end with an enlarged diameter. The housing 10 provides location for the liquid medication cartridge 100 and cartridge holder 20, windows for viewing the dose number on the number sleeve 60 and the gauge element 110, and a feature on its external surface, e.g. a circumferential groove, to axially retain the dose selector 80. An insert 12 comprises an inner thread engaging the piston rod 30. The housing 10 further has at least one internal, axially orientated slot or the like for axially guiding the gauge element 110. In the embodiment shown in the FIG., the distal end is provided with an axially extending strip partly overlapping cartridge holder 20. FIG. 2 depicts the housing 10 as a single housing characteristic. However, the housing 10 could comprise two or more housing characteristics which may be permanently attached to each other during assembly of the device. The drive spring 90 is attached with one end to the housing 10.

The cartridge holder 20 is located at the distal side of housing 10 and permanently attached thereto. The cartridge holder may be a transparent or translucent characteristic which is tubular to receive cartridge 100. The distal end of cartridge holder 20 may be provided with means for attaching a needle arrangement. A removable cap (not shown) may be provided to fit over the cartridge holder 20 and may be retained via clip features on the housing 10.

The piston rod 30 is rotationally constrained to the drive sleeve 40 via a splined interface. When rotated, the piston rod 30 is forced to move axially relative to the drive sleeve 40, through its threaded interface with the insert 12 of housing 10. The lead screw 30 is an elongate member with an outer thread engaging the corresponding thread of the insert 12 of housing 10. The interface comprises at least one longitudinal groove or track at the piston rod 30 and a corresponding protrusion or spline of the driver 40. At its distal end, the lead screw 30 is provided with an interface for clip attachment of the bearing 140.

The drive sleeve 40 is a hollow member surrounding the lead screw 30 and arranged within number sleeve 60. It extends from a ratchet interface with the clutch plate 120 to the contact with the clutch spring 130. The drive sleeve 40 is axially movable relative to the housing 10, the piston rod 30 and the number sleeve 60 in the distal direction against the bias of clutch spring 130 and in the opposite proximal direction under the bias of clutch spring 130. At least one longitudinal spline of the driver 40 engages a corresponding track of the lead screw 30.

Figure 4:
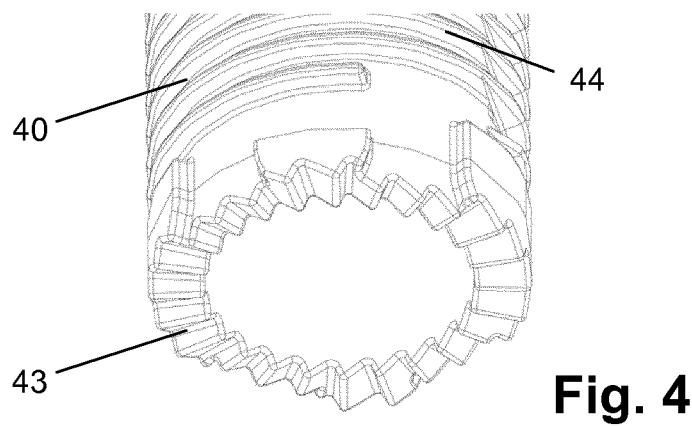
FIG. 4 shows a perspective side view of the drive sleeve of the device of FIG. 1.
Figure 5:
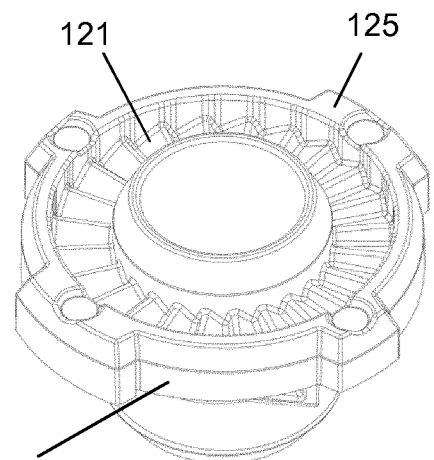
FIG. 5 shows a perspective side view of the clutch plate of the device of FIG. 1.

The ratchet or clutch interface between the drive sleeve 40 and the clutch plate 120 comprises a ring of pawl teeth 43 forming the pawl element according to the present disclosure located on the proximal end face of the drive sleeve 40 and a ring of corresponding gear teeth 121 forming the gear element according to the present disclosure located on the distal end face of the clutch plate 120 (see FIGS. 4 and 5).

A splined tooth interface 11, 42 with the housing 10 prevents rotation of the drive sleeve 40 during dose setting. This interface comprises a ring of radially extending outer teeth 42 at the distal end of drive sleeve 40 and corresponding radially extending inner teeth 11 of the housing characteristic 10. When the button 70 is pressed, these drive sleeve 40 to housing 10 spline teeth are disengaged allowing the drive sleeve 40 to rotate relative to housing 10. A further splined tooth interface with the number sleeve 60 is not engaged during dialling, but engages when the button 70 is pressed, preventing relative rotation between the drive sleeve 40 and number sleeve 60 during dispense. In a preferred embodiment this interface comprises inwardly directed splines on a flange on the inner surface of the number sleeve 60 and a ring of radially extending outer splines of drive sleeve 40. These corresponding splines are located on the number sleeve 60 and the drive sleeve 40, respectively, such that axial movement of the drive sleeve 40 relative to the (axially fixed) number sleeve 60 engages or disengages the splines to rotationally couple or decouple the drive sleeve 40 and the number sleeve 60.

The driver 40 has a threaded section providing a helical track for the nut 50, i.e. a thread 44. In addition, a last dose abutment or stop is provided which may be the end of the thread track or preferably a rotational hard stop for interaction with a corresponding last dose stop of nut 50, thus limiting movement of the nut 50 on the driver thread.

Figure 6:
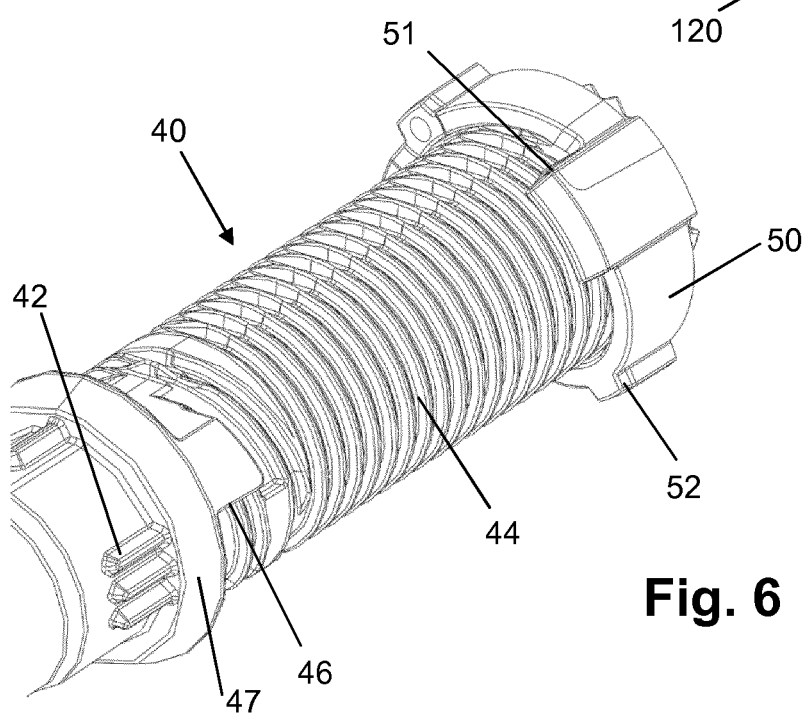
FIG. 6 shows another perspective side view of the drive sleeve of the device of FIG. 1.

The last dose nut 50 is located between the number sleeve 60 and the drive sleeve 40. It is rotationally constrained to the number sleeve 60, via a splined interface. It moves along a helical path relative to the drive sleeve 40, via a threaded interface (see thread 44 in FIG. 6), when relative rotation occurs between the number sleeve 60 and drive sleeve 40 which is during dialling only. As an alternative, the nut 50 may be splined to the driver 40 and threaded to the number sleeve 60. A last dose stop is provided on nut 50 engaging a stop of drive sleeve 40 when a dose is set corresponding to the remaining dispensable amount of medicament in the cartridge 100.

The dose indicator or number sleeve 60 is a tubular element. The number sleeve 60 is rotated during dose setting (via dose selector 80) and dose correction and during dose dispensing by torsion spring 90. The number sleeve 60 is axially constrained to the housing 10, e.g. by snap engagement of a bead on an inner housing surface with a groove on an outer number sleeve surface, while being free to rotate relative to the housing 10. The drive spring 90 is attached with one end to the number sleeve 60. Further, the number sleeve 60 is in threaded engagement with the gauge element 110 such that rotation of the number sleeve causes axial displacement of the gauge element 110. Together with gauge element 110 the number sleeve 60 defines a zero position ('at rest') and a maximum dose position. Thus, the number sleeve 60 may be seen as a dose setting member. The number sleeve 60 may comprise a number sleeve lower 60a which is rigidly fixed to a number sleeve upper 60b during assembly, e.g. by snap engagement, to form the number sleeve 60.

Clutch features which have the form of a ring of splines are provided inwardly directed on number sleeve upper 60b for engagement with splines of the button 70 during dose setting and dose correction. A clicker arm is provided on the outer surface of number sleeve 60 which interacts with the drive sleeve 40 and the gauge member 110 for generating a feedback signal. In addition, the number sleeve lower 60a is rotationally constrained to the nut 50 and to the clutch plate 120 via a splined interface comprising at least one longitudinal spline. Further, number sleeve lower 60a comprises an interface for attachment of the torsion spring 90.

Figure 3:
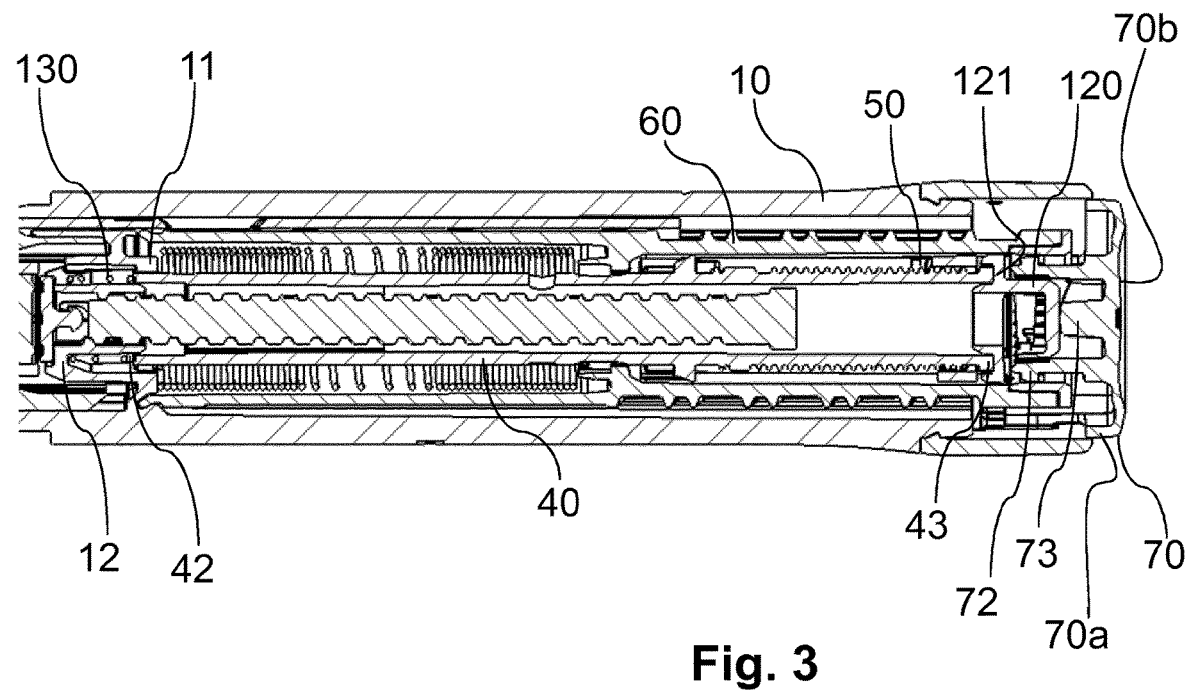
FIG. 3 shows a sectional view of the proximal end of the device of FIG. 1.

The button 70 forms the proximal end of the device. It may be beneficial if the button 70 is permanently splined to the dose selector 80 by a respective sleeve section 70a fixed at the rim of a plate-like body projecting into distal direction forming the touch surface 70b. A central stem 72 may extend distally from the proximal face of the plate-like body as it is shown in FIG. 3. The stem 72 is provided with a flange carrying the splines for engagement with splines of the number sleeve upper 60b. Thus, it is also splined via splines to the number sleeve upper 60b when the button 70 is not pressed, but this spline interface is disconnected when the button 70 is pressed. The button 70 may have a discontinuous annular skirt with splines. When the button 70 is pressed, splines on the button 70 engage with splines on the housing 10, preventing rotation of the button 70 (and hence the dose selector 80) during dispense. These splines disengage when the button 70 is released, allowing a dose to be dialled. The button further may comprise a central projection 73 projecting from the distal face of the plate-like body. The central projection 73 forms a central point support at the proximal surface of the clutch plate 120. During dose dispense the button 70 transmits the axial pressing force of the user via this central projection into distal direction to the clutch plate 120 against the bias of the clutch spring 130.

The dose selector 80 is axially constrained to the housing 10. It is rotationally constrained, via the splined interface, to the button 70. This splined interface which includes grooves interacting with spline features formed by the annular skirt of button 70 remains engaged irrespective of the dose button 70 axial positions. The dose selector 80 or dose dial grip is a sleeve-like characteristic with a serrated outer skirt.

The torsion spring 90 is attached at its distal end to the housing 10 and at the other end to the number sleeve 60. The torsion spring 90 is located inside the number sleeve 60 and surrounds a distal portion of the drive sleeve 40. The action of rotating the dose selector 80, to set a dose, rotates the number sleeve 60 relative to the housing 10, and charges the torsion spring 90 further.

The cartridge 100 is received in cartridge holder 20. The cartridge 100 may be a glass ampoule having a moveable rubber bung at its proximal end. The distal end of cartridge 100 is provided with a pierceable rubber seal which is held in place by a crimped annular metal band. In the embodiment depicted in the FIG., the cartridge 100 is a standard 1.5 ml cartridge. The device is designed to be disposable in that the cartridge 100 cannot be replaced by the user or health care professional. However, a reusable variant of the device could be provided by making the cartridge holder 20 removable and allowing backwinding of the lead screw 30 and the resetting of nut 50.

The gauge element 110 of FIGS. 1 and 2 is constrained to prevent rotation but allow translation relative to the housing 10 via a splined interface. The gauge element 110 has a helical feature on its inner surface which engages with the helical thread cut in the number sleeve 60 such that rotation of the number sleeve 60 causes axial translation of the gauge element 110. This helical feature on the gauge element 110 also creates stop abutments against the end of the helical cut in the number sleeve 60 to limit the minimum and maximum dose that can be set.

The gauge element 110 has a generally plate or band like characteristic having a central aperture or window and two flanges extending on either side of the aperture. The flanges are preferably not transparent and thus shield or cover the number sleeve 60, whereas the aperture or window allows viewing a portion of the number sleeve lower 60a. Further, gauge element 110 has a cam and a recess interacting with the clicker arm of the number sleeve 60 at the end of dose dispensing.

The clutch plate 120 (see FIG. 5) is a sleeve-like or ring-like characteristic. The clutch plate 120 is splined to the number sleeve 60 via outer splines 125. It is also coupled to the drive sleeve 40 via the ratchet interface comprising the pawl teeth 43 and the gear teeth 121. The ratchet teeth 43, 121 provide a detented position between the number sleeve 60 and drive sleeve 40 corresponding to each dose unit, and engages different ramped tooth angles during clockwise and anti-clockwise relative rotation. A clicker arm 123 may be provided on the clutch plate 120 for interaction with ratchet features of the button 70.

The clutch spring 130 is a compression spring. The axial position of the drive sleeve 40, clutch plate 120 and button 70 is defined by the action of the clutch spring 130, which applies a force on the drive sleeve 40 in the proximal direction. This spring force is reacted via the drive sleeve 40, clutch plate 120, and button 70, and when 'at rest' it is further reacted through the dose selector 80 to the housing 10. The spring force ensures that the ratchet interface between drive sleeve 40 and clutch plate 120 is always engaged. In the 'at rest' position, it also ensures that the button splines are engaged with the number sleeve splines, and the drive sleeve teeth 42 are engaged with inner teeth 11 of the housing 10 (see FIG. 3).

The bearing 140 is axially constrained to the piston rod 30 and acts on the bung within the liquid medicament cartridge. It is axially clipped to the lead screw 30, but free to rotate.

With the device in the 'at rest' condition as shown in FIG. 1, the number sleeve 60 is positioned against its zero dose abutment with the gauge element 110 and the button 70 is not depressed. Dose marking '0' on the number sleeve 60 is visible through the window of the housing 10 and gauge element 110, respectively.

The torsion spring 90, which has a number of pre-wound turns applied to it during assembly of the device, applies a torque to the number sleeve 60 and is prevented from rotating by the zero dose abutment.

The user selects a variable dose of liquid medicament by rotating the dose selector 80 clockwise, which generates an identical rotation in the number sleeve 60. Rotation of the number sleeve 60 causes charging of the torsion spring 90, increasing the energy stored within it. As the number sleeve 60 rotates, the gauge element 110 translates axially due to its threaded engagement thereby showing the value of the dialled dose. The gauge element 110 has flanges either side of the window area which cover the numbers printed on the number sleeve 60 adjacent to the dialled dose to ensure only the set dose number is made visible to the user.

The drug delivery device further may provide a visual feedback feature in addition to the discrete dose number display typical on devices of this type. The distal end of the gauge element 110 creates a sliding scale through the window in the housing 10. As an alternative, the sliding scale could be formed using a separate characteristic engaged with the number sleeve 60 on a different helical track.

As a dose is set by the user, the gauge element 110 translates axially, the distance moved proportional to the magnitude of the dose set. This feature gives clear feedback to the user regarding the approximate size of the dose set. The dispense speed of an auto-injector mechanism may be higher than for a manual injector device, so it may not be possible to read the numerical dose display during dispense. The gauge feature provides feedback to the user during dispense regarding dispense progress without the need to read the dose number itself. For example, the gauge display may be formed by an opaque element on the gauge element 110 revealing a contrasting coloured characteristic underneath. Alternatively, the revealable element may be printed with coarse dose numbers or other indices to provide more precise resolution. In addition, the gauge display simulates a syringe action during dose set and dispense.

The drive sleeve 40 is prevented from rotating as the dose is set and the number sleeve 60 rotated, due to the engagement of its splined teeth 42 with teeth 11 of the housing 10. Relative rotation must therefore occur between the clutch plate 120 and drive sleeve 40 via the ratchet clutch interface 43, 121.

The user torque required to rotate the dose selector 80 is a sum of the torque required to wind up the torsion spring 90, and the torque required to overhaul the ratchet clutch interface 43, 121. The clutch spring 130 is designed to provide an axial force to the ratchet clutch interface 43, 121 and to bias the clutch plate 120 onto the drive sleeve 40. This axial load acts to maintain the teeth engagement of the clutch plate 120 and drive sleeve 40. The torque required to overhaul the teeth 43, 121 in the dose set direction is a function of the axial load applied by the clutch spring 130, the clockwise ramp angle of the ratchet teeth 43, 121, the friction coefficient between the mating surfaces and the mean radius of the ratchet clutch interface 43, 121. When overrunning the pawl teeth 43 of the drive sleeve 40 the clutch plate 120 vibrates back and forth into axial direction wherein the gear teeth 121 of the clutch plate hit the side faces of the pawl teeth 43 producing a clicking noise symbolizing one dose unit which is often perceived too loud. Inventive measures to reduce this noise, i.e. a noise reduction characteristic at at least a part of the surface of the pawl element and/or the gear element are described in detail below referring to FIGS. 7 to 34.

As the user rotates the dose selector 80 sufficiently to increment the mechanism by one increment (one dose unit), the clutch plate 120 rotates relative to the drive sleeve 40 by one ratchet tooth 43, 121. At this point the ratchet teeth re-engage into the next detented position. An audible click is generated by the ratchet re-engagement, and tactile feedback is given by the change in torque input required.

Relative rotation of the number sleeve 60 and the drive sleeve 40 is allowed. This relative rotation also causes the last dose nut 50 to travel along its threaded path, towards its last dose abutment on the drive sleeve 40.

With no user torque applied to the dose selector 80, the number sleeve 60 is now prevented from rotating back under the torque applied by the torsion spring 90, solely by the ratchet clutch interface 43, 121 between the clutch plate 120 and the drive sleeve 40. The torque necessary to overhaul the ratchet clutch 43, 121 in the anti-clockwise direction is a function of the axial load applied by the clutch spring 130, the anti-clockwise ramp angle of the ratchet 43, 121, the friction coefficient between the mating surfaces and the mean radius of the ratchet clutch features 43, 121. The torque necessary to overhaul the ratchet clutch 43, 121 must be greater than the torque applied to the number sleeve 60 (and hence clutch plate 120) by the torsion spring 90. The ratchet ramp angle is therefore increased in the anti-clockwise direction to ensure this is the case whilst ensuring the dial-up torque is as low as possible.

The user may now choose to increase the selected dose by continuing to rotate the dose selector 80 in the clockwise direction. The process of overhauling the ratchet clutch interface 43, 121 between the number sleeve 60 and drive sleeve 40 is repeated for each dose increment. Additional energy is stored within the torsion spring 90 for each dose increment and audible and tactile feedback is provided for each increment dialled by the re-engagement of the ratchet teeth. The torque required to rotate the dose selector 80 increases as the torque required to wind up the torsion spring 90 increases. The torque required to overhaul the ratchet clutch 43, 121 in the anti-clockwise direction must therefore be greater than the torque applied to the number sleeve 60 by the torsion spring 90 when the maximum dose has been reached.

If the user continues to increase the selected dose until the maximum dose limit is reached, the number sleeve 60 engages with its maximum dose abutment on the maximum dose abutment of gauge element 110. This prevents further rotation of the number sleeve 60, clutch plate 120 and dose selector 80.

Depending on how many increments have already been delivered by the mechanism, during selection of a dose, the last dose nut 50 may contact its last dose abutment with stop face of the drive sleeve 40. The abutment prevents further relative rotation between the number sleeve 60 and the drive sleeve 40, and therefore limits the dose that can be selected. The position of the last dose nut 50 is determined by the total number of relative rotations between the number sleeve 60 and drive sleeve 40, which have occurred each time the user sets a dose.

With the mechanism in a state in which a dose has been selected, the user is able to deselect (correct) any number of increments from this dose. Deselecting a dose is achieved by the user rotating the dose selector 80 anti-clockwise. The torque applied to the dose selector 80 by the user is sufficient, when combined with the torque applied by the torsion spring 90, to overhaul the ratchet interface 43, 121 between the clutch plate 120 and drive sleeve 40 in the anti-clockwise direction. When the ratchet clutch 43, 121 is overhauled, anti-clockwise rotation occurs in the number sleeve 60 (via the clutch plate 120), which returns the number sleeve 60 towards the zero dose position, and unwinds the torsion spring 90. The relative rotation between the number sleeve 60 and drive sleeve 40 causes the last dose nut 50 to return along its helical path, away from the last dose abutment.

With the mechanism in a state in which a dose has been selected, the user is able to activate the mechanism to commence delivery of a dose. Delivery of a dose is initiated by the user depressing the button 70 axially in the distal direction.

When the button 70 is depressed using the touch surface 70b, splines between the button 70 and number sleeve 60 are disengaged, rotationally disconnecting the button 70 and dose selector 80 from the delivery mechanism, i.e. from number sleeve 60, gauge element 110 and torsion spring 90. Splines on the button 70 engage with splines on the housing 10, preventing rotation of the button 70 (and hence the dose selector 80) during dispense. As the button 70 is stationary during dispense, it can be used in the dispense clicker mechanism. A stop feature in the housing 10 limits axial travel of the button 70 and reacts any axial abuse loads applied by the user, reducing the risk of damaging internal characteristics.

The clutch plate 120 and drive sleeve 40 travel axially with the button 70. This engages the splined tooth interface 43, 121 between the clutch plate 120 and number sleeve 60, preventing relative rotation between the drive sleeve 40 and number sleeve 60 during dispense. The splined tooth interface 11, 42 between the drive sleeve 40 and the housing 10 disengages, so the drive sleeve 40 can now rotate and is driven by the torsion spring 90 via the number sleeve 60, and clutch plate 120.

Rotation of the drive sleeve 40 causes the piston rod 30 to rotate due to their splined engagement, and the piston rod 30 then advances due to its threaded engagement to the housing 10. The number sleeve 60 rotation also causes the gauge element 110 to traverse axially back to its zero position whereby the zero dose abutment stops the mechanism.

Tactile feedback during dose dispense may be provided via the compliant cantilever clicker arm integrated into the clutch plate 120. This arm interfaces radially with ratchet features on the inner surface of the button 70, whereby the ratchet tooth spacing corresponds to the number sleeve 60 rotation required for a single increment dispense. During dispense, as the number sleeve 60 rotates and the button 70 is rotationally coupled to the housing 10, the ratchet features engage with the clicker arm to produce an audible click with each dose increment delivered.

Delivery of a dose continues via the mechanical interactions described above while the user continues to depress the button 70. If the user releases the button 70, the clutch spring 130 returns the drive sleeve 40 to its 'at rest' position (together with the clutch plate 120 and button 70), engaging the splines between the drive sleeve 40 and housing 10, preventing further rotation and stopping dose delivery.

During delivery of a dose, the drive sleeve 40 and number sleeve 60 rotate together, so that no relative motion in the last dose nut 50 occurs. The last dose nut 50 therefore travels axially relative to the drive sleeve 40 during dialling only.

Once the delivery of a dose is stopped, by the number sleeve 60 returning to the zero dose abutment, the user may release the button 70, which will re-engage the spline teeth 11, 42 between the drive sleeve 40 and housing 10. The mechanism is now returned to the 'at rest' condition.

At the end of dose dispensing, additional audible feedback is provided in the form of a 'click', distinct from the 'clicks' provided during dispense, to inform the user that the device has returned to its zero position via the interaction of the clicker arm on the number sleeve 60 with the ramp on the drive sleeve 40 and the cam and the recess on the gauge element 110. This embodiment allows feedback to only be created at the end of dose delivery and not created if the device is dialled back to, or away from, the zero position.

Figure 9:
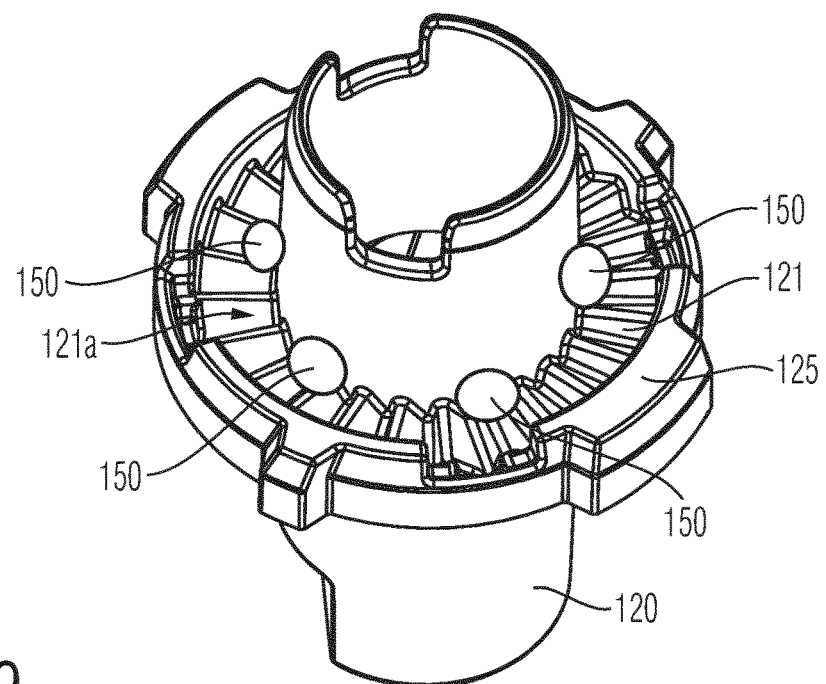
FIG. 9 shows another sectional view of the clutch plate of FIG. 5.

A first embodiment of a noise reductions characteristic is shown in FIGS. 1 to 9, particularly in FIGS. 7 to 9. In this embodiment at an inner section 43a of the pawl teeth 43 of the drive sleeve 40 and an inner section 121a of the gear teeth 121 of the clutch plate 120 grease 150 is applied in multiple spots around the circumference of the clutch plate 120 and drive sleeve 40 proximal face. The inner section is a section close to the longitudinal axis of the drive mechanism. The grease 150 moves into the detents of the pawl teeth 43 and the gear teeth 121 and decelerates the movement of the teeth when overrunning the ratchet structure caused by the viscosity of the grease 150. Accordingly, loudness of noise is reduced. Further, the friction between the inner surface 40a of the drive sleeve 40 and the outer surface 120a of the axial stem of the clutch plate 120 is reduced by the grease 150 flowing into the space marked in FIG. 8 by reference number 43b. This further reduces noise and enhances the ratchet movement.

Figure 10:
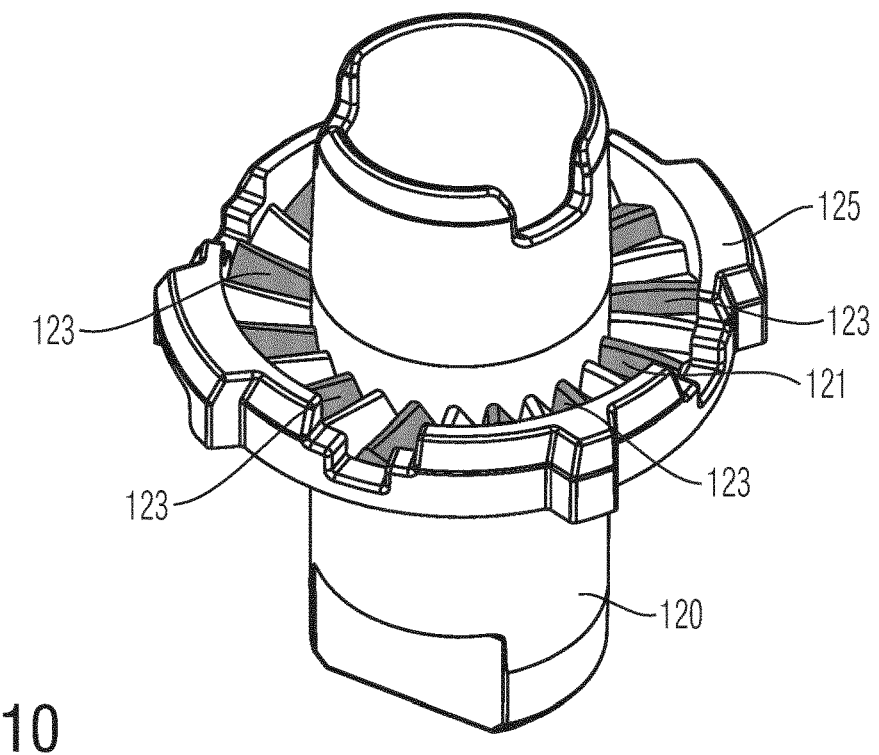
FIG. 10 shows a perspective side view of a clutch plate of a second embodiment of a drive mechanism.

A second embodiment of a noise reduction characteristic is shown in FIG. 10. In this embodiment the noise characteristic comprises a surface layer 123 consisting of elastomeric material at a part of the surface of the gear teeth 121. In the embodiment shown in FIG. 10 the front side, the back side and the upper side of each second gear tooth 121 is covered with the surface layer 123 ensuring that the initial contact of the pawl teeth 43 is with the soft, elastomeric surface. The soft surface layer 123 reduces the time for which the noise rings out and thereby reduces loudness. Other distribution of the elastomeric surface layer (e.g.

every third tooth, only at the front side or at the back side of each predefined gear tooth) is possible as well. Alternatively, the surface layer 123 consisting of elastomeric material may be provided at the pawl teeth 43. The elastomeric surface layer 123 may cover the teeth surface of teeth 121, 43 over their full length in radial direction or over part of this length, for example based on considerations at which section of the teeth in radial direction the impact of the overrunning teeth is first or with the highest force.

In a third embodiment the noise reduction characteristic comprises helical gear teeth 221 and corresponding helical pawl teeth 243 shown in FIGS. 11 to 13. The drive sleeve 40 further comprises grouped pawl teeth 243 comprising two clusters of five teeth 243 and alternating two clusters of three teeth 243. Using helical teeth 221, 243 the contact area spreads gradually as the teeth 221, 243 move closer together thereby spreading the impact of the ratchet over a longer time period and distribute the load more evenly. This reduces the amplitude of the sound emitted at this interface.

Figure 14:
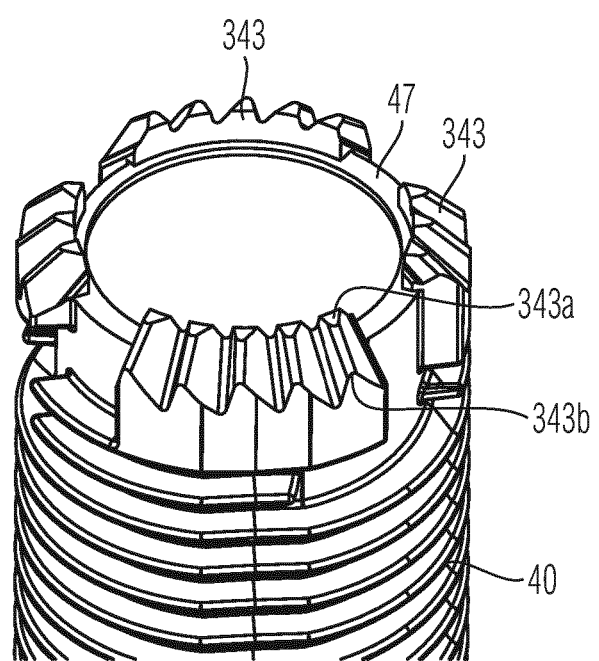
FIG. 14 shows a perspective side view of a drive sleeve of a fourth embodiment of a drive mechanism.

Turning now to FIG. 14, a fourth embodiment of the noise reduction characteristic comprises beveled teeth. FIG. 14 shows the drive sleeve 40 comprising beveled pawl teeth 343, wherein the height of the teeth at the inner section 343*a* is greater than the height of the teeth 343 at the outer section 343*b* of each tooth along the radial direction. As in the previous embodiment the drive sleeve 40 comprises grouped pawl teeth 343 with two clusters of five teeth 343 and alternating two clusters of three teeth 343. The gear teeth (not shown) of the clutch plate have a complementary form. As in the previous embodiment the impact of the ratchet of this embodiment is spread over a longer time period as well, thereby reducing the amplitude of sound emitted at this interface.

Figure 15:
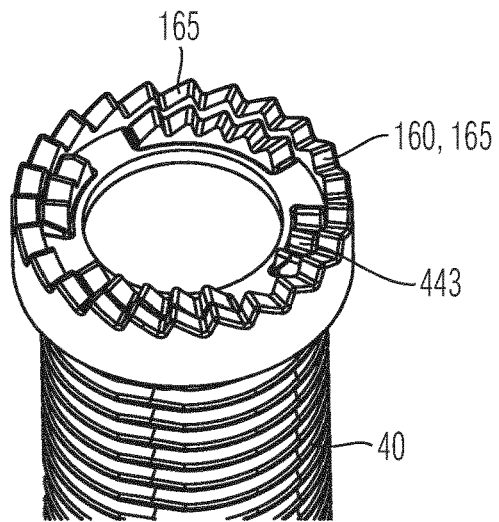
FIG. 15 shows a perspective side view of a drive sleeve of a fifth embodiment of a drive mechanism with an annular collar.
Figure 17:
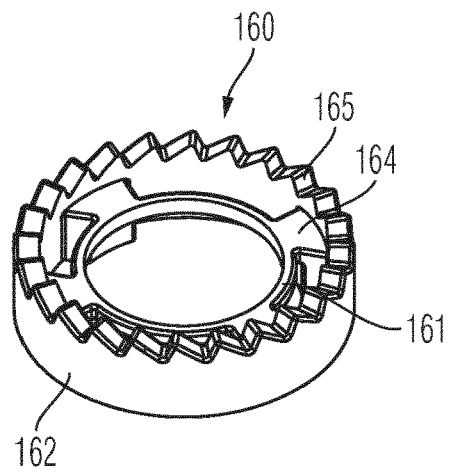
FIG. 17 shows a perspective side view of the annular collar of FIG. 15.
Figure 16:
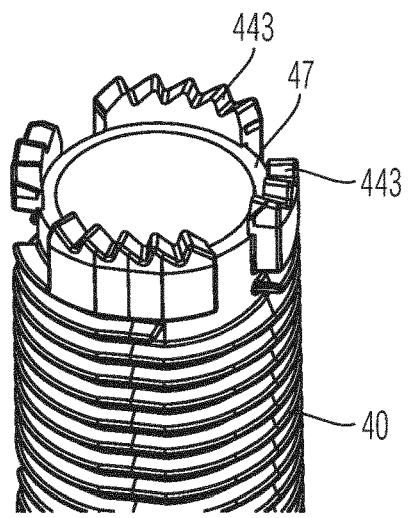
FIG. 16 shows a perspective side view of the drive sleeve of FIG. 15.

Another embodiment of a noise reduction characteristic is shown in FIGS. 15 to 17. Therein, the drive sleeve 40 comprises an annular collar 160 consisting of elastomeric material which is attached at the proximal end of the drive sleeve 40. The annular collar 160 comprises an inner ring (or hollow cylinder) 161 and an outer ring (or hollow cylinder) 162, wherein the inner ring 161 and the outer ring 162 are arranged concentrically. The inner ring 161 is attached at the outer ring 162 by means of four radial webs 164. Further, a number of collar teeth 165 are located at the upper surface (front surface) of the outer ring 162 such that they partly complete the pawl teeth 443 of the drive sleeve 40. Accordingly, the pawl teeth 443 of the drive sleeve are shortened compared with the embodiment of FIG. 4, for example. At the location of each radial web 164 of the annular collar 160 the teeth of the drive sleeve are removed. Each tooth of the pawl element of this embodiment forms a combined tooth consisting of the material of the drive sleeve 40 at its inner section and of the material of the annular collar 160 at its outer section with regard to its radial length. The combined teeth 443, 165 may be formed straight, helically or beveled as described above. As in the previous embodiment the drive sleeve 40 comprises grouped pawl teeth 443 comprising two clusters of five teeth 443 and alternating two clusters of three teeth 443. The form of the gear teeth of the clutch plate corresponds to the form of the combined pawl teeth 443, 165. This embodiment maximizes damping by ensuring interference with a full annular profile of teeth.

Figure 18:
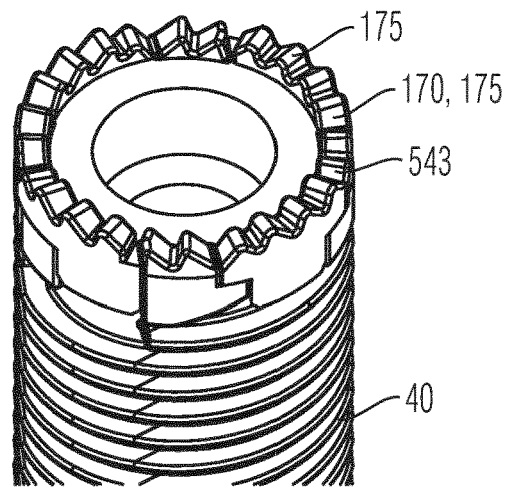
FIG. 18 shows a perspective side view of a drive sleeve of a sixth embodiment of a drive mechanism with an internal bung.
Figure 20:
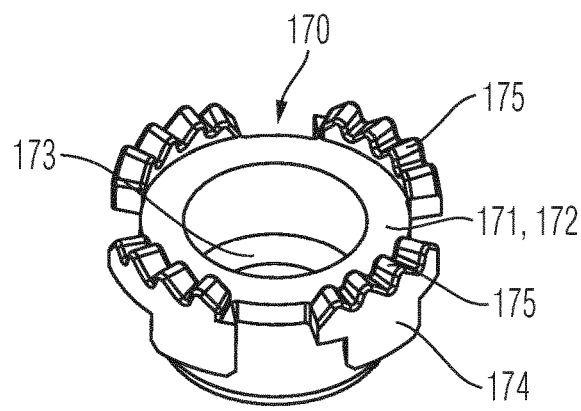
FIG. 20 shows a perspective side view of the internal bung of FIG. 18.
Figure 19:
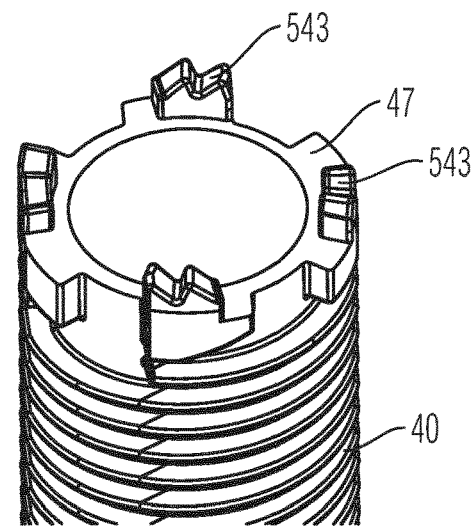

The next embodiment of a noise reduction characteristic is shown in FIGS. 18 to 20. Therein, the drive sleeve 40 comprises an internal bung 170 consisting of elastomeric material which is attached at the proximal end of the drive sleeve 40. The internal bung 170 comprises a pot-like circular body 171 which is formed as a U in cross-section with a cylindrical section 172 and a plate-like base section 173. The bung further may have a flange-like section 174 at its outer rim in order to fix the bung 170 at the drive sleeve 40. Further, a number of bung teeth 175 are located at the upper surface (front surface) of the cylindrical section 172 such that they complete the pawl teeth 543 of the drive sleeve 40 together forming a full circumference. The teeth 543, 175 may be formed straight, helically or beveled as described above. The drive sleeve 40 comprises grouped pawl teeth 543 comprising four clusters of two teeth 543 and alternating with four clusters of four bung teeth 175. The form of the gear teeth of the clutch plate corresponds to the form of the teeth 543, 175. This embodiment ensures good noise reduction by damping of the elastomeric material of the bung teeth 175 and additionally provides an improvement in robustness of the drive mechanism.

Figure 21:
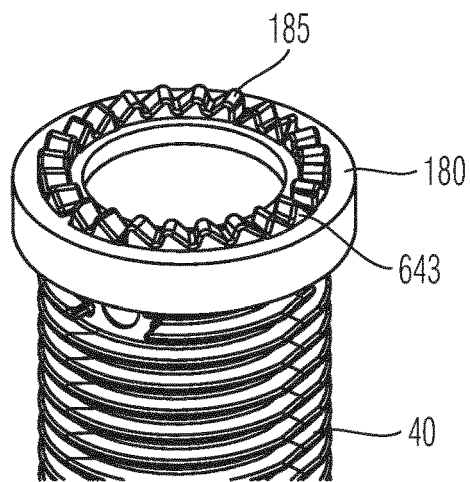
FIG. 21 shows a perspective side view of a drive sleeve of a seventh embodiment of a drive mechanism with a damping hoop.
Figure 23:
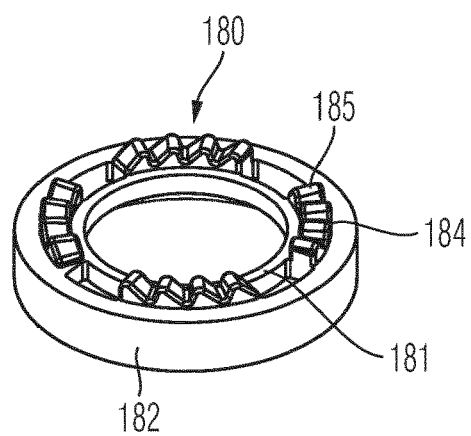
FIG. 23 shows a perspective side view of the damping hoop of FIG. 21.
Figure 22:
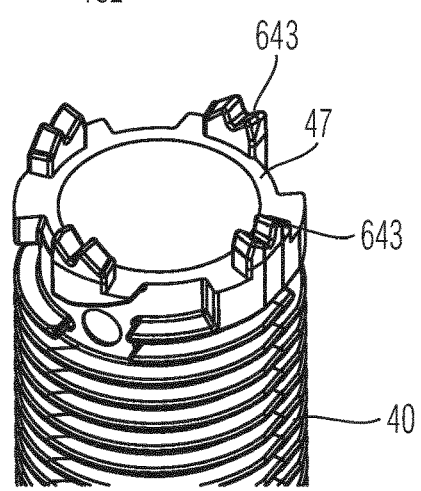
FIG. 22 shows a perspective side view of the drive sleeve of FIG. 21.
Figure 24:
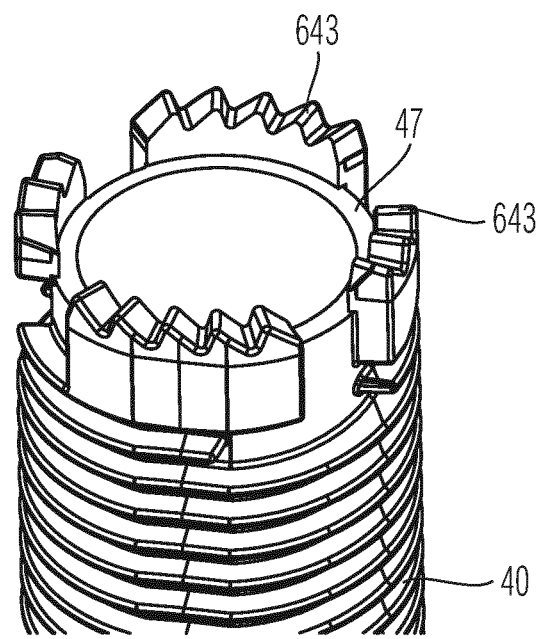
FIG. 24 shows a perspective side view of a drive sleeve relating to the embodiment of FIG. 21 with a different number of teeth.

Another embodiment of a noise reduction characteristic shown in FIGS. 21 to 23 comprises a damping hoop 180. Therein, the damping hoop 180 consists of elastomeric material which is attached at the proximal end of the drive sleeve 40. The damping hoop 180 comprises an inner ring (or hollow cylinder) 181 and an outer ring (or hollow cylinder) 182, wherein the inner ring 181 and the outer ring 182 are arranged concentrically. The inner ring 181 is attached at the outer ring 182 by means of four radial webs 184. Further, a number of collar teeth 185 are located at the upper surface (front surface) of the radial webs 184 such that they complete the pawl teeth 643 of the drive sleeve 40 together forming a full circumference. The pawl teeth 643 project through the cavities between the outer ring 182 and the inner ring 181. The teeth 643, 185 may be formed straight, helically or beveled as described above. The drive sleeve 40 comprises grouped pawl teeth 643 comprising four clusters of two teeth 643 and alternating with four clusters of four hoop teeth 185. The form of the gear teeth of the clutch plate corresponds to the form of the teeth 643, 185. This embodiment has a solid outer geometry formed by the outer ring 182 which strengthens the damping feature.

Figure 25:
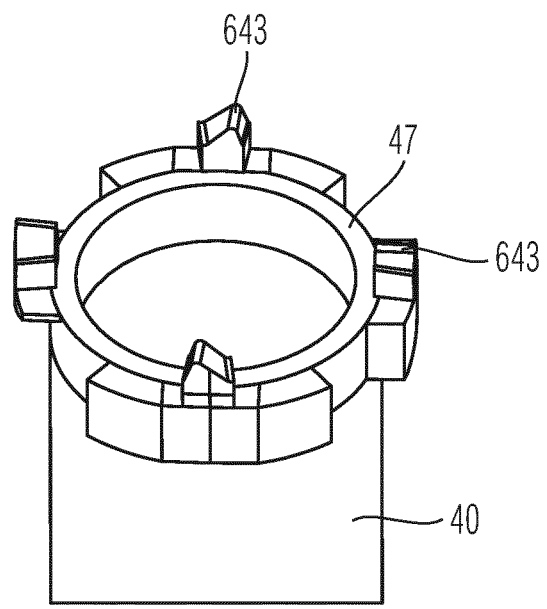
FIG. 25 shows a perspective side view of another drive sleeve relating to the embodiment of FIG. 21 with a different number of teeth.

Concerning the embodiments depicted in FIGS. 11 to 25 the drive sleeve 40 in each case comprises a proximal end section 47 formed as a hollow cylinder, wherein the pawl teeth 243, 343, 443, 543, 643 are located at the outer surface (shell face) of this end section 47, wherein the most proximal section of the pawl teeth 243, 343, 443, 543, 643 exceed in height over the proximal face of the proximal end section 47. The pawl teeth 243, 343, 443, 543, 643 may be grouped in clusters of two, three, four (see FIG. 24), five or more pawl teeth, wherein each cluster has a certain pre-defined distance from the next cluster along the outer rim of the end section 47. Additionally, single pawl teeth may be attached to the outer surface of the end section 47 of the drive sleeve as shown in FIG. 25 as well.

Figure 26:
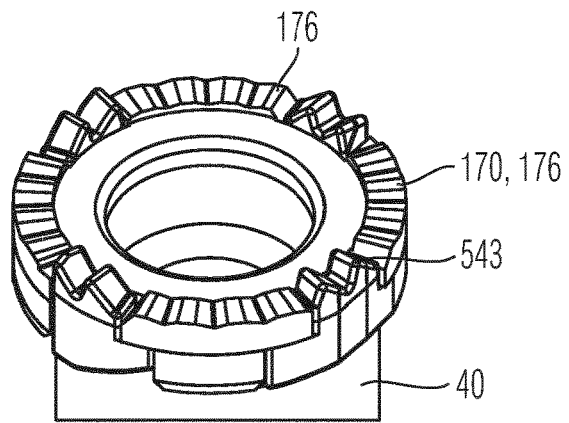
FIG. 26 shows a perspective side view of a drive sleeve of an eighth embodiment of a drive mechanism with an internal bung.
Figure 27:
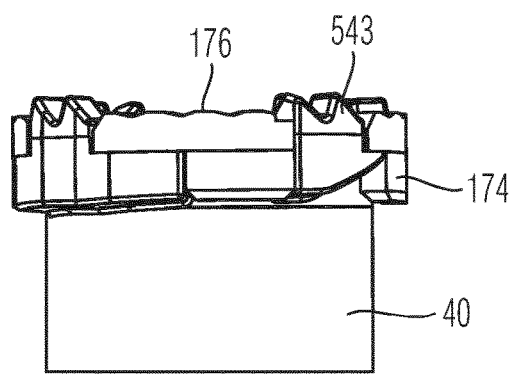
FIG. 27 shows a perspective side view of the drive sleeve with internal bung of FIG. 26.
Figure 28:
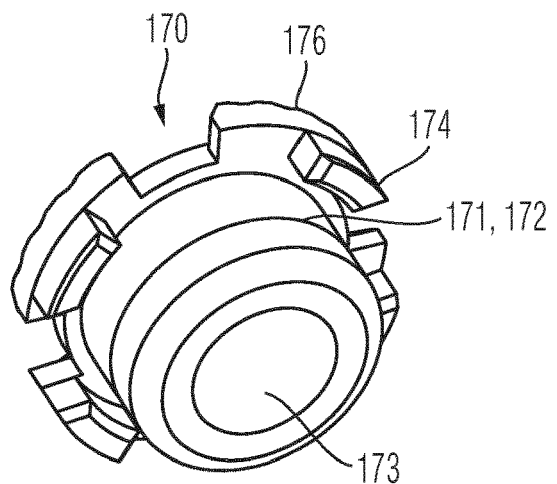
FIG. 28 shows a perspective side view of the internal bung of FIG. 26.

The embodiment shown in FIGS. 26 to 28 is similar to the embodiment of FIGS. 18 to 20, wherein each cluster of bung teeth 175 is replaced by a cuboid projection 176 with notches 177. Each bung teeth 175 is replaced by a notched section projecting from the upper surface of the bung 170. The projection runs along the circumference of the bung 170.

Figure 29:
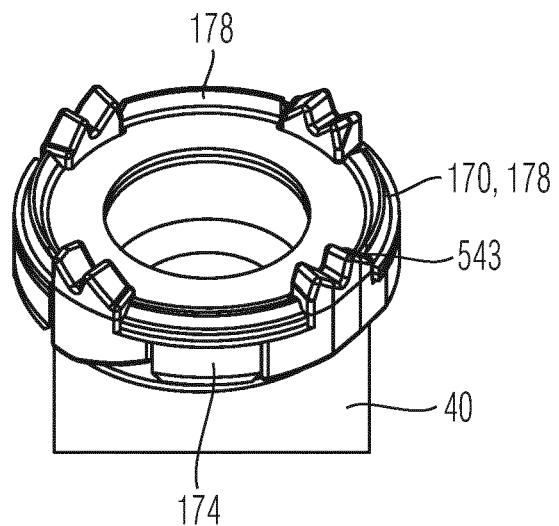
FIG. 29 shows a perspective side view of a drive sleeve of an nineth embodiment of a drive mechanism with an internal bung.
Figure 30:
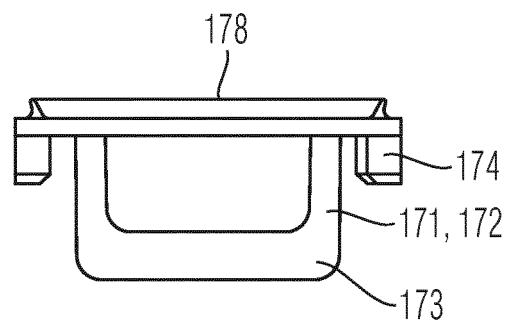
FIG. 30 shows a sectional view of the internal bung of FIG. 29.
Figure 31:
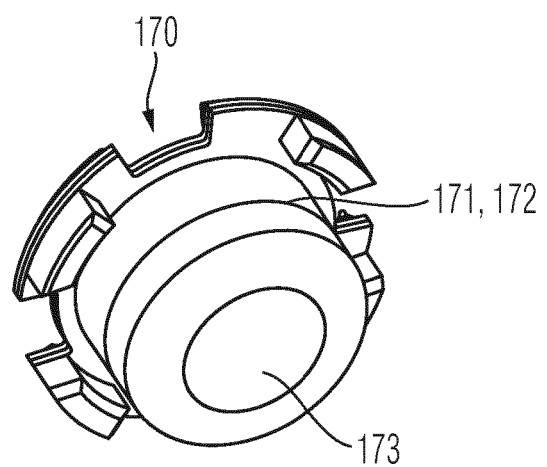
FIG. 31 shows a perspective side view of the internal bung of FIG. 29.

The embodiment shown in FIGS. 29 to 31 is similar to the embodiment of FIGS. 18 to 20, wherein each cluster of bung teeth 175 is replaced by a compressible lip 178 (crab claw section) projecting from the upper end face (proximal end face) of the bung 170. The lip 178 runs along a circumference of the bung interrupted by the pawl teeth 543. The cross-sectional width of the lip 178 is less than the wall width of the cylindrical section 172 of the bung 170.

Figure 32:
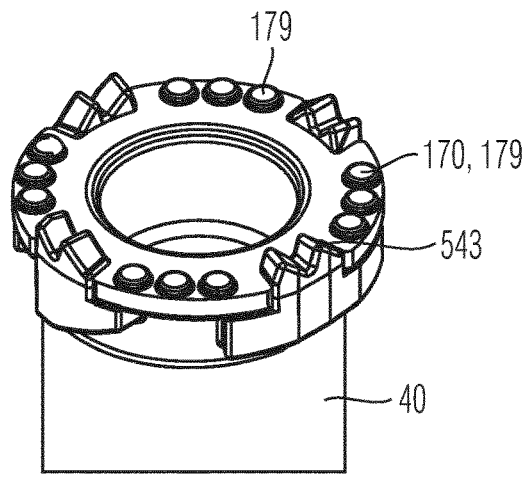
FIG. 32 shows a perspective side view of a drive sleeve of a tenth embodiment of a drive mechanism with an internal bung.
Figure 33:
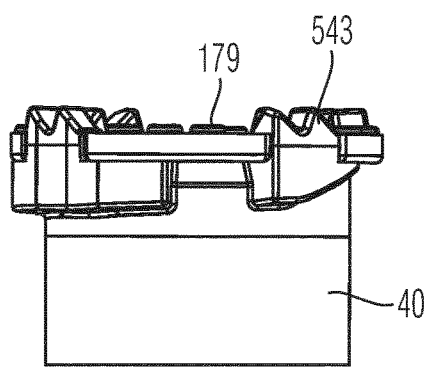
FIG. 33 shows a perspective side view of the drive sleeve with internal bung of FIG. 32.
Figure 34:
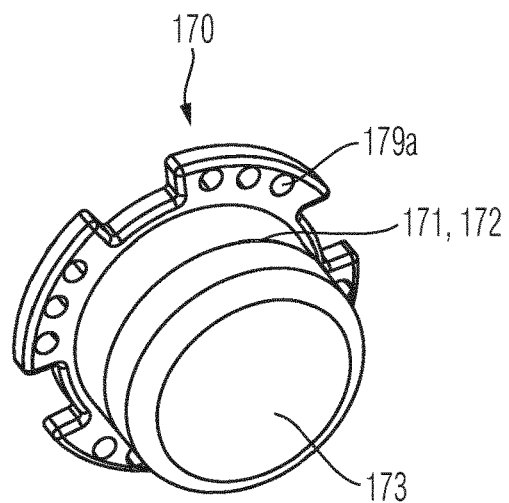
FIG. 34 shows a perspective side view of the internal bung of FIG. 32.

The embodiment shown in FIGS. 32 to 34 is similar to the embodiment of FIGS. 18 to 20, wherein each bung tooth 175 is replaced by a pebble projection 179 projecting from the upper end face (proximal end face) of the bung 170. The row of pebble projections 179 runs along a circumference of the bung interrupted by the pawl teeth 543. The pebble projection 179 projects from the upper end face of the bung 170 and is formed like a cut pebble or a cut sphere.

The above embodiments cuboid projection 176, lip 178 and pebble projection 179 may replace at least partly the teeth 165 of the annular ring 160 or the teeth 185 of the damping hoop 180 as well. At the lower side of a flange section of the cylindrical section 172 of the bung 170 there is a plurality of recesses 179a accommodated around the circumference of the bung 170 which match with respective projections at the proximal end face of the drive sleeve 40 in order to rotationally fix the bung 170 at the drive sleeve 40.

REFERENCE NUMERALS 10 housing (casing)
11 spline tooth
12 insert
20 cartridge holder
30 piston rod (lead screw)
40 drive sleeve
40a inner surface of drive sleeve 40
42 spline tooth
43 pawl tooth
43a inner section of pawl tooth
44 thread
47 proximal end section
50 nut
60 dose setting element
60a number sleeve lower
60b number sleeve upper
70 button
70a sleeve section
70b touch surface
72 stem
73 central projection
80 dose selector
90 torsion spring
100 cartridge
110 gauge element
120 clutch plate
120a outer surface of clutch plate stem
121 gear tooth
121a inner section of gear tooth
123 surface layer of the gear tooth 121
130 clutch spring
140 bearing
150 grease
160 annular collar
161 inner ring
162 outer ring
164 radial web
165 collar tooth
170 internal bung
171 body
172 cylindrical section
173 plate-like section
174 flange-like section
175 bung tooth
176 projection
178 lip
179 pebble projection
179a recess
180 damping hoop
181 inner ring
182 outer ring
184 radial web
185 hoop tooth
223 helical gear tooth
243 helical pawl tooth
343 beveled pawl tooth
343a inner section of beveled pawl tooth
343b outer section of beveled pawl tooth
443 pawl tooth
543 pawl tooth
643 pawl tooth

The invention claimed is:

1. A drive mechanism for a drug delivery device, the drive mechanism comprising:
a dose selector; and
a housing and a ratchet with a gear element comprising a plurality of gear teeth connected with the dose selector and a pawl element rotationally constrained to the housing comprising at least one pawl tooth,
wherein the at least one pawl tooth engages with the plurality of gear teeth and is located opposite to the plurality of gear teeth,
wherein one of the gear element and the pawl element moves forth and back relative to the other element of the gear element and the pawl element along a first direction for de-engagement and re-engagement of opposite gear teeth and the at least one pawl tooth when the gear element rotates relative to the housing during dose setting using the dose selector,
wherein one or both of the pawl element and the gear element comprises a noise reduction characteristic at a surface which dampens noise produced when a tooth or teeth of a respective other element of the pawl element and the gear element moves or move back into re-engagement when the gear element rotates relative to the pawl element,
wherein the noise reduction characteristic comprises at least one of:
a helical form of the plurality of gear teeth and a corresponding helical form of the at least one pawl tooth,
a beveled form of the plurality of gear teeth and a corresponding beveled form of the at least one pawl tooth, and
an elastomeric material surface layer or an elastomeric material body at a predefined section of one or both of at least part of the plurality of gear teeth and the at least one pawl tooth.

2. The drive mechanism of claim 1, wherein the first direction is a longitudinal direction of the drive mechanism or a direction radial to the longitudinal direction.

3. The drive mechanism of claim 1, wherein the pawl element is located at a front face of a drive sleeve.

4. The drive mechanism of claim 3, wherein the drive sleeve is rotationally constrained with respect to the housing during dose setting.

5. The drive mechanism of claim 1, wherein the plurality of gear teeth are located at a front face of a clutch plate that is rotationally constrained with respect to the dose selector during dose setting.

6. The drive mechanism of claim 1, wherein the noise reduction characteristic comprises grease located at the surface of the plurality of gear teeth or the at least one pawl tooth at an inner section.

7. The drive mechanism of claim 1, wherein the noise reduction characteristic comprises an annular collar attached at the gear element or at the pawl element with a plurality of pawl teeth.

8. The drive mechanism of claim 7, wherein the annular collar comprises a plurality of collar teeth formed by an elastomeric material.

9. The drive mechanism of claim 8, wherein the collar teeth form an outer section of at least a part of the plurality of gear teeth or the plurality of pawl teeth.

10. The drive mechanism of claim 1, wherein the noise reduction characteristic comprises an internal bung attached at the gear element or at the pawl element with a plurality of pawl teeth.

11. The drive mechanism of claim 10, wherein the internal bung comprises a plurality of bung teeth elements formed by an elastomeric material.

12. The drive mechanism of claim 11, wherein the plurality of bung teeth elements forms the at least one of the plurality of gear teeth or the plurality of pawl teeth.

13. The drive mechanism of claim 12, wherein the plurality of bung teeth elements and the plurality of hoop teeth elements comprise one of a straight tooth corresponding in a form to a tooth, a notched section, a crab claw section, and a pebble projection.

14. The drive mechanism of claim 1, wherein the noise reduction characteristic comprises a damping hoop attached at the gear element or at the pawl element with a plurality of pawl teeth.

15. The drive mechanism of claim 14, wherein the damping hoop comprises a plurality of hoop teeth elements formed by an elastomeric material.

16. The drive mechanism of claim 15, wherein the plurality of hoop teeth elements forms the at least one of the plurality of gear teeth or the plurality of pawl teeth.

17. The drive mechanism of claim 16, wherein the plurality of bung teeth elements and the plurality of hoop teeth elements comprise one of a straight tooth corresponding in a form to a tooth, a notched section, a crab claw section, and a pebble projection.

18. A drug delivery device comprising:
the drive mechanism comprising:
a dose selector; and
a housing and a ratchet with a gear element comprising a plurality of gear teeth connected with the dose selector and a pawl element rotationally constrained to the housing comprising at least one pawl tooth,
wherein the at least one pawl tooth engages with the plurality of gear teeth and is located opposite to the plurality of gear teeth,
wherein one of the gear element and the pawl element moves forth and back relative to the other element of the gear element and the pawl element along a first direction for de-engagement and re-engagement of opposite gear teeth and the at least one pawl tooth when the gear element rotates relative to the housing during dose setting using the dose selector,
wherein one or both of the pawl element and the gear element comprises a noise reduction characteristic at a surface which dampens noise produced when a tooth or teeth of a respective other element of the pawl element and the gear element moves or move back into re-engagement when the gear element rotates relative to the pawl element,
wherein the noise reduction characteristic comprises at least one of:
a helical form of the plurality of gear teeth and a corresponding helical form of the at least one pawl tooth,
a beveled form of the plurality of gear teeth and a corresponding beveled form of the at least one pawl tooth, and
an elastomeric material surface layer or an elastomeric material body at a predefined section of one or both of at least part of the plurality of gear teeth and the at least one pawl tooth.

19. The drug delivery device of claim 18, wherein the first direction is a longitudinal direction of the drive mechanism or a direction radial to the longitudinal direction.

20. The drug delivery device of claim 18, wherein the pawl element is located at a front face of a drive sleeve.

* * * * *